(12) United States Patent
Sorensen et al.

(10) Patent No.: US 11,291,584 B2
(45) Date of Patent: Apr. 5, 2022

(54) DUAL BLADE OPHTHALMOLOGIC SURGERY DEVICE

(71) Applicant: Microsurgical Technology, Inc., Redmond, WA (US)

(72) Inventors: John T. Sorensen, Lake Elsinore, CA (US); Michael Mittelstein, Laguna Niguel, CA (US); Soheila Mirhashemi, Laguna Niguel, CA (US)

(73) Assignee: MICROSURGICAL TECHNOLOGY, INC., Redmond, WA (US)

( * ) Notice: Subject to any disclaimer, the term of this patent is extended or adjusted under 35 U.S.C. 154(b) by 0 days.

(21) Appl. No.: 17/115,922

(22) Filed: Dec. 9, 2020

(65) Prior Publication Data

US 2021/0113380 A1    Apr. 22, 2021

Related U.S. Application Data

(60) Continuation of application No. 15/714,909, filed on Sep. 25, 2017, now Pat. No. 10,888,460, which is a division of application No. 15/076,624, filed on Mar. 21, 2016, now Pat. No. 9,820,885, which is a continuation of application No. 14/789,632, filed on Jul. 1, 2015, now Pat. No. 9,358,155, which is a continuation of application No. 14/481,754, filed on (Continued)

(51) Int. Cl.
| | | |
|---|---|---|
| *A61F 9/007* | (2006.01) | |
| *A61B 18/14* | (2006.01) | |
| *A61B 17/32* | (2006.01) | |
| *A61B 18/00* | (2006.01) | |

(52) U.S. Cl.
CPC .. *A61F 9/00781* (2013.01); *A61B 17/320016* (2013.01); *A61B 18/1482* (2013.01); *A61F 9/007* (2013.01); *A61F 9/0079* (2013.01); *A61F 9/00736* (2013.01); *A61B 2017/320064* (2013.01); *A61B 2018/00083* (2013.01); *A61B 2018/1497* (2013.01)

(58) Field of Classification Search
None
See application file for complete search history.

(56) References Cited

U.S. PATENT DOCUMENTS

| | | |
|---|---|---|
| 421,855 A | 2/1890 | Burk |
| 637,463 A | 11/1899 | Hegarty |

(Continued)

FOREIGN PATENT DOCUMENTS

| | | |
|---|---|---|
| EP | 0073803 A1 | 3/1983 |
| EP | 1455698 A1 | 9/2004 |

(Continued)

OTHER PUBLICATIONS

International Search Report and Written Opinion received for PCT Patent Application No. PCT/US2004/018488, dated Oct. 4, 2005, 4 pages.

(Continued)

*Primary Examiner* — Amy R Weisberg
(74) *Attorney, Agent, or Firm* — Wiley Rein LLP

(57) ABSTRACT

A dual blade device and method useable for performing an ab interno procedure within a human eye to remove a strip of trabecular meshwork tissue.

7 Claims, 3 Drawing Sheets

Related U.S. Application Data

Sep. 9, 2014, now Pat. No. 9,107,729, which is a division of application No. 13/159,356, filed on Jun. 13, 2011, now abandoned, which is a division of application No. 10/560,267, filed as application No. PCT/US2004/018488 on Jun. 10, 2004, now Pat. No. 7,959,641.

(60) Provisional application No. 60/477,258, filed on Jun. 10, 2003.

(56) References Cited

U.S. PATENT DOCUMENTS

| | | | |
|---|---|---|---|
| 2,130,949 | A | 9/1938 | Wharton |
| 2,220,169 | A | 11/1940 | Murdock |
| 2,364,333 | A | 12/1944 | Wisher |
| 3,294,085 | A | 12/1966 | Wallace |
| 3,365,798 | A | 1/1968 | Cunningham |
| 3,776,238 | A | 12/1973 | Peyman et al. |
| 3,882,872 | A | 5/1975 | Douvas et al. |
| 3,972,117 | A | 8/1976 | Fogg |
| 4,011,869 | A | 3/1977 | Seiler, Jr. |
| 4,111,207 | A | 9/1978 | Seiler, Jr. |
| 4,255,854 | A | 3/1981 | Bilbao |
| 4,365,957 | A | 12/1982 | Das |
| 4,428,748 | A | 1/1984 | Peyman et al. |
| 4,472,879 | A | 9/1984 | Sizemore, Jr. |
| 4,501,274 | A | 2/1985 | Skjaerpe |
| 4,559,942 | A | 12/1985 | Eisenberg |
| 4,577,629 | A | 3/1986 | Martinez |
| 4,649,919 | A | 3/1987 | Thimsen et al. |
| 4,689,040 | A | 8/1987 | Thompson |
| 4,706,669 | A | 11/1987 | Schlegel |
| 4,712,546 | A | 12/1987 | Noe |
| 4,753,234 | A | 6/1988 | Martinez |
| 4,759,746 | A | 7/1988 | Straus |
| 4,841,984 | A | 6/1989 | Armeniades et al. |
| 4,900,300 | A | 2/1990 | Lee |
| 4,955,883 | A | 9/1990 | Nevyas et al. |
| 4,955,887 | A | 9/1990 | Zirm |
| 5,019,035 | A | 5/1991 | Missirlian et al. |
| 5,042,008 | A | 8/1991 | Iwasa et al. |
| 5,112,299 | A | 5/1992 | Pascaloff |
| 5,123,904 | A | 6/1992 | Shimomura et al. |
| 5,163,433 | A | 11/1992 | Kagawa et al. |
| 5,222,959 | A | 6/1993 | Anis |
| 5,224,950 | A | 7/1993 | Prywes |
| 5,269,782 | A | 12/1993 | Sutter |
| 5,284,472 | A | 2/1994 | Sussman et al. |
| 5,431,646 | A | 7/1995 | Vassiliadis et al. |
| 5,431,671 | A | 7/1995 | Nallakrishnan |
| 5,458,596 | A | 10/1995 | Lax et al. |
| 5,478,338 | A | 12/1995 | Reynard |
| 5,487,747 | A | 1/1996 | Stegmann et al. |
| 5,529,580 | A | 6/1996 | Kusunoki et al. |
| 5,540,706 | A | 7/1996 | Aust et al. |
| 5,540,708 | A | 7/1996 | Lim et al. |
| 5,558,637 | A | 9/1996 | Allonen et al. |
| 5,569,283 | A | 10/1996 | Green et al. |
| 5,681,282 | A | 10/1997 | Eggers et al. |
| 5,733,297 | A | 3/1998 | Wang |
| 5,755,716 | A | 5/1998 | Garito et al. |
| 5,807,277 | A | 9/1998 | Swaim |
| 5,817,115 | A | 10/1998 | Nigam |
| 5,843,106 | A | 12/1998 | Heisler |
| 5,865,831 | A | 2/1999 | Cozean et al. |
| 5,885,279 | A | 3/1999 | Bretton |
| 5,922,003 | A | 7/1999 | Anctil et al. |
| 5,957,881 | A | 9/1999 | Peters et al. |
| 5,957,914 | A | 9/1999 | Cook et al. |
| 5,964,777 | A | 10/1999 | Drucker |
| 6,004,199 | A | 12/1999 | Habenicht et al. |
| 6,013,049 | A | 1/2000 | Rockley et al. |
| 6,068,629 | A | 5/2000 | Haissaguerre et al. |
| 6,213,997 | B1 | 4/2001 | Hood et al. |
| 6,217,598 | B1 | 4/2001 | Berman et al. |
| 6,241,721 | B1 | 6/2001 | Cozean et al. |
| 6,251,103 | B1 | 6/2001 | Berlin |
| 6,264,668 | B1 | 7/2001 | Prywes |
| 6,283,961 | B1 | 9/2001 | Underwood et al. |
| 6,290,699 | B1 | 9/2001 | Hall et al. |
| 6,293,957 | B1 | 9/2001 | Peters et al. |
| 6,382,974 | B1 | 5/2002 | Garfinkel |
| 6,388,043 | B1 | 5/2002 | Langer et al. |
| 6,419,684 | B1 | 7/2002 | Heisler et al. |
| 6,428,501 | B1 | 8/2002 | Reynard |
| 6,428,539 | B1 | 8/2002 | Baxter et al. |
| 6,432,104 | B1 | 8/2002 | Durgin et al. |
| 6,497,712 | B1 | 12/2002 | Feaster |
| RE38,018 | E | 3/2003 | Anctil et al. |
| 6,557,258 | B1 | 5/2003 | Roberts et al. |
| 6,720,402 | B2 | 4/2004 | Langer et al. |
| 6,759,481 | B2 | 7/2004 | Tong |
| 6,979,328 | B2 | 12/2005 | Baerveldt et al. |
| 7,131,975 | B2 | 11/2006 | Adams |
| 7,244,256 | B2 | 7/2007 | Decesare et al. |
| 7,374,566 | B1 | 5/2008 | Schossau |
| 7,604,663 | B1 | 10/2009 | Reimink et al. |
| 7,632,303 | B1 | 12/2009 | Stalker et al. |
| 7,648,591 | B2 | 1/2010 | Furst et al. |
| 7,785,321 | B2 | 8/2010 | Baerveldt et al. |
| 7,842,034 | B2 | 11/2010 | Mittelstein et al. |
| 7,935,131 | B2 | 5/2011 | Anthamatten et al. |
| 7,955,387 | B2 | 6/2011 | Richter |
| 7,959,641 | B2 | 6/2011 | Sorensen et al. |
| 8,038,923 | B2 | 10/2011 | Berger et al. |
| 8,069,546 | B1 | 12/2011 | Whittemore |
| 8,147,424 | B2 | 4/2012 | Kassab et al. |
| 9,107,729 | B2 | 8/2015 | Sorensen et al. |
| 9,358,155 | B2 | 6/2016 | Sorensen et al. |
| 9,820,885 | B2 | 11/2017 | Sorensen et al. |
| 10,327,947 | B2 | 6/2019 | Kahook |
| 10,786,391 | B2 | 9/2020 | Kahook |
| 2001/0034932 | A1 | 11/2001 | Macdonald |
| 2001/0053873 | A1 | 12/2001 | Schaaf et al. |
| 2002/0002372 | A1 | 1/2002 | Jahns et al. |
| 2002/0026205 | A1 | 2/2002 | Matsutani et al. |
| 2002/0038129 | A1 | 3/2002 | Peters et al. |
| 2002/0111608 | A1 | 8/2002 | Baerveldt et al. |
| 2003/0208217 | A1 | 11/2003 | Dan |
| 2004/0127927 | A1* | 7/2004 | Adams .............. A61B 17/26 606/170 |
| 2004/0138685 | A1 | 7/2004 | Clague et al. |
| 2004/0153111 | A1 | 8/2004 | Hosoada |
| 2004/0204732 | A1 | 10/2004 | Muchnik |
| 2004/0210245 | A1 | 10/2004 | Erickson et al. |
| 2005/0090849 | A1 | 4/2005 | Adams |
| 2005/0159767 | A1 | 7/2005 | Adams et al. |
| 2006/0095055 | A1 | 5/2006 | Douglas et al. |
| 2006/0106370 | A1 | 5/2006 | Baerveldt et al. |
| 2006/0149194 | A1 | 7/2006 | Conston et al. |
| 2006/0149267 | A1 | 7/2006 | Nordt |
| 2006/0200180 | A1 | 9/2006 | Lee |
| 2006/0212060 | A1 | 9/2006 | Hacker et al. |
| 2006/0241580 | A1 | 10/2006 | Mittelstein et al. |
| 2007/0010812 | A1 | 1/2007 | Mittelstein et al. |
| 2007/0073275 | A1 | 3/2007 | Conston et al. |
| 2007/0149974 | A1 | 6/2007 | Mangione |
| 2007/0276420 | A1 | 11/2007 | Sorensen et al. |
| 2008/0077146 | A1 | 3/2008 | Pernsteiner et al. |
| 2009/0248141 | A1 | 10/2009 | Shandas et al. |
| 2009/0287233 | A1 | 11/2009 | Huculak |
| 2011/0077626 | A1 | 3/2011 | Baerveldt et al. |
| 2011/0230877 | A1 | 9/2011 | Huculak et al. |
| 2012/0071908 | A1 | 3/2012 | Sorensen et al. |
| 2012/0083727 | A1 | 4/2012 | Barnett |
| 2012/0123533 | A1 | 5/2012 | Shiuey |
| 2012/0191120 | A1 | 7/2012 | Linsi |
| 2014/0379015 | A1 | 12/2014 | Sorensen et al. |
| 2015/0045820 | A1 | 2/2015 | Kahook |
| 2015/0297400 | A1 | 10/2015 | Sorensen et al. |
| 2016/0220418 | A1 | 8/2016 | Sorensen et al. |
| 2018/0125712 | A1 | 5/2018 | Sorensen et al. |

(56) References Cited

U.S. PATENT DOCUMENTS

FOREIGN PATENT DOCUMENTS

| EP | 1615604 A1 | 1/2006 |
|---|---|---|
| EP | 1631204 A2 | 3/2006 |
| EP | 2303203 A1 | 4/2011 |
| JP | S4625677 Y1 | 9/1971 |
| KR | 20040058309 A | 7/2004 |
| WO | 91/17793 A1 | 11/1991 |
| WO | 98/27876 A1 | 7/1998 |
| WO | 01/78631 A2 | 10/2001 |
| WO | 02/056805 A2 | 7/2002 |
| WO | 03/045290 A1 | 6/2003 |
| WO | 2004/093761 A1 | 11/2004 |
| WO | 2004/110501 A2 | 12/2004 |
| WO | 2009/140185 A1 | 11/2009 |
| WO | 2011/030081 A1 | 3/2011 |
| WO | 2013/163034 A1 | 10/2013 |

OTHER PUBLICATIONS

Supplementary European Search Report received for European Patent Application No. 04754925.8 dated Jan. 16, 2009, 5 pages.
Anderson, Douglas R., "Trabeculotomy Compared to Goniotomy for Glaucoma in Children", Ophthalmology, vol. 90, No. 7, Jul. 1983, pp. 805-806.
Dominguez A., "Ab Interno Trabeculotomy", Bulletins et memoires de la Societe francaise, vol. 86, 1973.
Francis et al., "Ab Interno Trabeculectomy: Development of a Novel Device (Trabectome™) and Surgery for Open-Angle Glaucoma", Journal of Glaucoma, vol. 15, No. 1, Mar. 2006, pp. 68-73.
Grant, W. M., "Clinical Measurements of Aqueous Outflow", AMA Archives of Ophthalmology, vol. 46, No. 2, 1951, pp. 113-131.
Grant, Morton, "Experimental Aqueous Perfusion in Enucleated Human Eyes", Archives of Ophthalmology, vol. 69, No. 6, Jun. 1963, pp. 783-801.
Herschler et al., "Modified Goniotomy for Inflammatory Glaucoma, Histologic Evidence for the Mechanism of Pressure Reduction", Archives of Ophthalmology, vol. 98, No. 4, Apr. 1980, pp. 684-687.
Jacobi et al., "Goniocurettage for Removing Trabecular Meshwork: Clinical Results of a New Surgical Technique in Advanced Chronic Open-Angle Glaucoma", American Journal of Ophthalmology, vol. 127, No. 5, May 1999, pp. 505-510.
Jacobi et al., "Technique of Goniocurettage: A Potential Treatment for Advanced Chronic open Angle Glaucoma", British Journal of Ophthalmology, vol. 81, No. 4, 1997, pp. 302-307.
Jea et al., "Ab Interno Trabeculectomy Versus Trabeculectomy for Open-Angle Glaucoma", Ophthalmology, vol. 119, No. 1, Jan. 2012, pp. 36-42.
Johnson et al., "Human Trabecular Meshwork Organ Culture. A New Method", Investigative Ophthalmology & Visual Science, vol. 28, No. 6, Jun. 1987, pp. 945-953.
Luntz et al., "Trabeculotomy Ab Externo and Trabeculectomy in Congenital and Adult-Onset Glaucoma", American Journal of Ophthalmology, vol. 83, No. 2, Feb. 1977, pp. 174-179.
Minckler et al., "Clinical Results With the Trabectome for Treatment of Open-Angle Glaucoma", Ophthalmology, vol. 112, No. 6, Jun. 2005, pp. 962-967.
Pantcheva et al., "Ab Interno Trabeculectomy", Middle East African Journal of Ophthalmology, vol. 17, No. 4, 2010, pp. 287-289.
Quigley et al., "The number of people with glaucoma worldwide in 2010 and 2020", British Journal of Ophthalmology, vol. 90, 2006, pp. 262-267.
Quintana, "Gonioscopic Trabeculotomy. First Results", Second European Glaucoma Symposium, Helsinki, 1984, pp. 265-271.
Seibold et al., "Preclinical Investigation of Ab Interno Trabeculectomy Using a Novel Dual-Blade Device", The American Journal of Ophthalmology, vol. 155, No. 3, 2013, pp. 524-529.
Skjaerpe, F., "Selective Trabeculectomy. A Report of a New Surgical Method for Open Angle Glaucoma", ACTA Ophthalmologica, vol. 61, 1983, pp. 714-727.
Soohoo et al., "Ab Interno Trabeculectomy in the Adult Patient", Middle East African Journal of Ophthalmology, vol. 22, No. 1, Jan.-Mar. 2, pp. 25-29.
Tan et al., "Postoperative Complications After Glaucoma Surgery for Primary Angle-Closure Glaucoma vs Primary Open-Angle Glaucoma", Archives of Ophthalmology, vol. 129, No. 8, Aug. 2011, pp. 987-992.
Ting et al., "Ab Interno Trabeculectomy: Outcomes in Exfoliation Versus Primary Open-Angle Glaucoma", Journal of Cataract & Refractive Surgery, vol. 38, No. 2, Feb. 2012, pp. 315-323.
International Preliminary Report on Patentability received for PCT Patent Application No. PCT/US2004/018488, dated Dec. 13, 2005, 4 pages.
Phillip C. Jacobi et al., "Perspectives in trabecular surgery," Eye 2000;14(Pt 3B)(3b):519-530 (2000).
E. Ferrari et al., "Ab-interno trabeculo-canalectomy: surgical approach and histological examination," European J. Ophthalmology 12(5):401-05 (2002).
T. Shute, "A Novel Technique for Ab Interne Trabeculectomy: Description of Procedure and Preliminary Results," Am. Glaucoma Society 29th Annual Meeting Poster Abstracts 34-35 (2019)(available at: https://ags.planion.com/Web.User/AbstractDet?ACCOUNT=AGS&CONF=AM 19&ABSID=12309).
Transcript of Deposition of Dr. Peter Netland (Sep. 30, 2021).
A. Arora et al., "K-RIM (Corneal Rim) Angle Surgery Training Model," J Glaucoma 28(2):146-49 (Feb. 2019).
Bernard Becker, M.D. et al., "Symposium: microsurgery of the outflow channels. Clinical research." Trans Am Acad Gphthalmol Otolaryngol. Mar.-Apr. 1972;76(2):405-10. PMID: 4582683.
William H. Spencer, M.D., "Symposium: microsurgery of the outflow channels. Histological evaluation of microsurgical glaucoma techniques." Trans Am Acad Ophthalmol Otolaryngol. Mar.-Apr. 1972;76(2):389-397. PMID: 4270305.
Jonathan Herschler, M.D., et al., "Modified Goniotomy for Inflammatory Glaucoma: Histologic Evidence for the Mechanism of Pressure Reduction." Arch Ophthalmol. 1980;98(4):684-687.
Harold G. Scheie, M.D., "Stripping of Descemet's Membrane in Cataract Extraction," Tr. Am. Opth. Soc., vol. 62, 140-152(1964).
Richard S. Snell et al., Clinical Anatomy of the Eye, Malden, Massachusetts: Blackwell Science, Inc. (2nd ed., 1998).
Am. Acad. Of Ophthalmology, Section 8 External Disease and Cornea, in Basic and Clinical Science Course 2001-2002 (2001) ("AAO Cornea").
Michael John Hogan, History of the Human Eye: An Atlas and Textbook. Philadelphia, Pennsylvania: W. B. Saunders Company (1971).
M. Bruce Shields, Textbook of Glaucoma, Fourth Edition. Baltimore, Maryland: Williams & Wilkins (1998).
Am. Acad. Of Ophthalmology, Section 10 Glaucoma, in Basic and Clinical Science Course 2000-2001 (2000).
Erin G. Sieck et al., Outcomes of Kahook Dual blade Goniotomy with and without Phacoemulsification Cataract Extraction, 1 Ophthalmology Glaucoma, 75-81 (2018).
Todd Neff, UCHealth Eye Center lands global innovation awards, UCHealth Today, Jan. 6, 2016.
Presentation by New World Medical titled "KDB Competitive: Trabectome/Goniotome {MST}".
Oct. 21, 2015 press release titled "New World Medical to Launch the Kahook Dual Blade at AAO Meeting".
University of Colorado a global leader in patents for inventions, innovations, CU Connections, Jun. 1, 2020.
KDB Glide comparison to the TrabEx.
Dorland's Medical Dictionary Shorter Edition abridged from 25th ed. (1980) excerpt at 605 (definition of "section").
Blacks Medical Dictionary 47th ed. (1992) excerpt at 519 (definition of "section").
Declaration of Dr. Peter Netland submitted in 2020.
Reply Declaration of Dr. Peter Netland submitted in 2021.
Deposition Transcript of Deposition of Garry Condon, M.D., Tuesday, Aug. 17, 2021.
Deposition Transcript of Deposition of Garry Condon, M.D., Tuesday, Aug. 18, 2021.
Transcript of Oral argument conducted on Jan. 10, 2022.

(56) References Cited

OTHER PUBLICATIONS

Declaration of Garry P. Condon, M.D. submitted in 2021.
Transcript of Deposition of Dr. Peter Netland (May 27, 2021).
Transcript of Deposition of Dr. Peter Netland (May 28, 2021).

* cited by examiner

DUAL BLADE OPHTHALMOLOGIC SURGERY DEVICE

RELATED APPLICATIONS

This application is a continuation of copending U.S. patent application Ser. No. 15/714,909 filed Sep. 25, 2017, which is a division of U.S. patent application Ser. No. 15/076,624 filed Mar. 21, 2016 and issued as U.S. Pat. No. 9,820,885 on Nov. 21, 2017, which is a continuation of U.S. patent application Ser. No. 14/789,632 filed Jul. 1, 2015 and issued as U.S. Pat. No. 9,358,155 on Jun. 7, 2016, which is a continuation of U.S. patent application Ser. No. 14/481,754 filed Sep. 9, 2014 and issued as U.S. Pat. No. 9,107,729 on Aug. 18, 2015, which is a division of U.S. patent application Ser. No. 13/159,356 filed Jun. 13, 2011 and now abandoned, which is a division of U.S. patent application Ser. No. 10/560,267 filed May 11, 2006 and issued as U.S. Pat. No. 7,959,641 on Jun. 14, 2011, which is a 35 U.S.C. § 371 national stage of PCT International Patent Application No. PCT/US2004/018488 filed Jun. 10, 2004, which claims priority to U.S. Provisional Patent Application No. 60/477,258 filed on Jun. 10, 2003, the entire disclosure of each such prior patent and application being expressly incorporated herein by reference.

BACKGROUND OF THE INVENTION

There are numerous medical and surgical procedures in which it is desirable to cut and remove a strip of tissue of controlled width from the body of a human or veterinary patient. For example, it may sometimes be desirable to form an incision of a controlled width (e.g., an incision that is wider than an incision made by a typical scalpel or cutting blade) in the skin, mucous membrane, tumor, organ or other tissue or a human or animal. Also, it may sometimes desirable to remove a strip or quantity of tissue from the body of a human or animal for use as a biopsy specimen, for chemical/biological analysis, for retention or archival of DNA identification purposes, etc. Also, some surgical procedures require removal of a strip of tissue of a known width from an anatomical location within the body of a patient.

One surgical procedure wherein a strip of tissue of a known width is removed from an anatomical location within the body of a patient is an ophthalmological procedure used to treat glaucoma. This ophthalmological procedure is sometimes referred to as a goniectomy. In a goniectomy procedure, a device that is operative to cut or ablate a strip of tissue of approximately 2-10 mm in length and about 50-200 μm in width is inserted into the anterior chamber of the eye and used to remove a full thickness strip of tissue from the trabecular meshwork. The trabecular meshwork is a loosely organized, porous network of tissue that overlies a collecting canal known as Schlemm's canal. A fluid, known as aqueous humor, is continually produced in the anterior chamber of the eye. In normal individuals, aqueous humor flows through the trabecular meshwork, into Schlemm's Canal and out of the eye through a series of ducts. In patients who suffer from glaucoma, the drainage of aqueous humor from the eye may be impaired by elevated flow resistance through the trabecular meshwork, thereby resulting in an increase in intraocular pressure. The goniectomy procedure can restore normal drainage of aqueous humor from the eye by removing a full thickness segment of the trabecular meshwork, thus allowing the aqueous humor to drain through the open area from which the strip of trabecular meshwork has been removed. The goniectomy procedure and certain prior art instruments useable to perform such procedure are described in U.S. patent application Ser. No. 10/052,473 published as No. 2002/011608A1 (Baerveldt), the entirety of which is expressly incorporated herein by reference.

At present there remains a need in the art for the development of simple, inexpensive and accurate instruments useable to perform the goniectomy procedure as well as other procedures where it is desired to remove a strip of tissue from a larger mass of tissue.

SUMMARY OF THE INVENTION

The present invention provides a device for cutting a strip of tissue of approximate width W from a mass of tissue. The device generally comprises a) an elongate cutting tube that has a distal end and a lumen that opens through an opening in the distal end and b) first and second cutting edges formed on generally opposite edges of the distal end of the cutting tube and separated by a distance D. The cutting tube is advanceable through tissue such that the first and second cutting edges will cut a strip of tissue having approximate width W, wherein the approximate width W is approximately equal to the distance D between the first and second cutting edges. In some embodiments, the strip of tissue may be aspirated or otherwise removed through the lumen of the cutter tube. In some embodiments, the device may include apparatus useable to sever (e.g., transversely cut or transect) the strip of tissue when the strip of tissue has reached a desired length.

Further in accordance with the invention there is provided a method for cutting a strip of tissue of width W from a tissue mass. This method generally comprises the steps of a) providing a device that comprises i) an elongate cutting tube that has a distal end and a lumen that opens through an opening in the distal end and ii) first and second cutting edges formed on generally opposite edges of the distal end of the cutting tube and separated by a distance D that is approximately equal to the width W of the strip of tissue to be cut; and b) advancing the distal end of the cutting tube through the mass of tissue such that the first and second cutting edges cut a strip of tissue of approximate width W. Further aspects and elements of the invention will be understood by those of skill in the art upon reading the detailed description of specific examples set forth here below.

DETAILED DESCRIPTION

Figure 1:
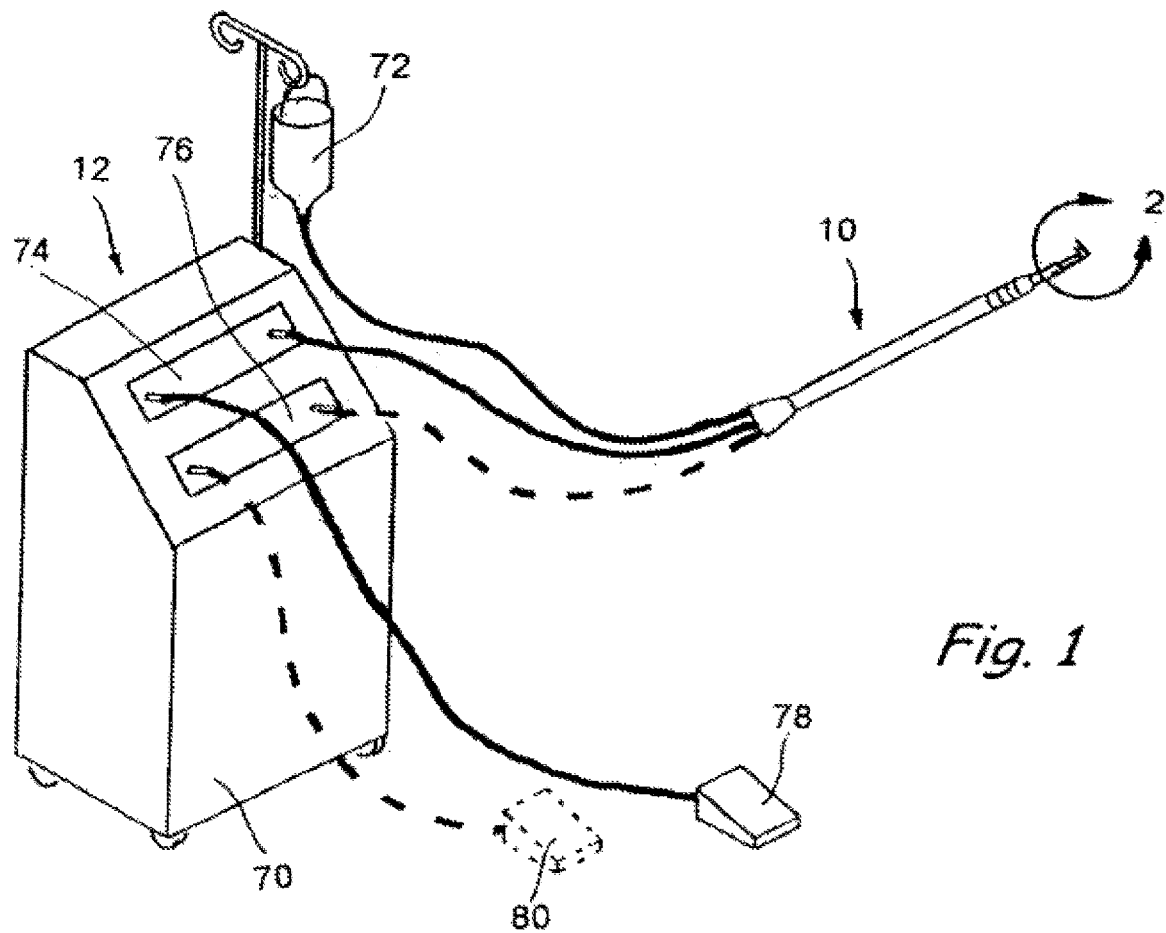
FIG. 1 is a perspective view of a system incorporating a needle cutting device of the present invention.
Figure 2:
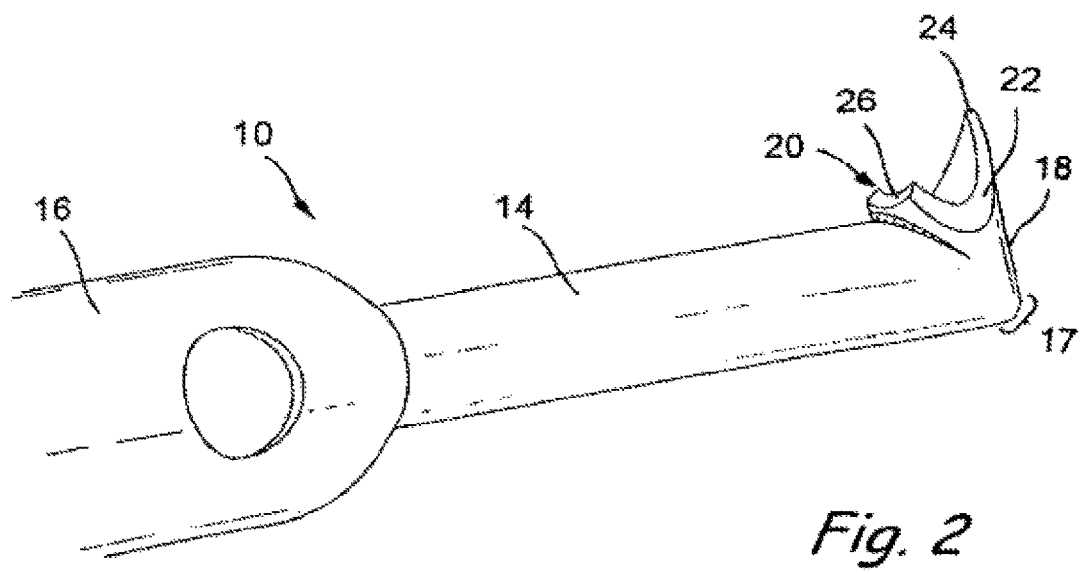
FIG. 2 is an enlarged perspective view of section 2 of FIG. 1.

The following detailed description, and the drawings to which it refers, are provided for the purpose of describing and illustrating certain preferred embodiments or examples of the invention only, and no attempt has been made to exhaustively describe all possible embodiments or examples of the invention. Thus, the following detailed description and the accompanying drawings shall not be construed to limit, in any way, the scope of the claims recited in this patent application and any patent(s) issuing therefrom.

One example of a needle cutter device 10 of the present invention is shown in FIGS. 1-4. This needle cutter device 10 generally comprises an elongate cutting tube 14 that has a distal end and a lumen 27 that opens through an opening in the distal end. First and second cutting edges 20, 22 are formed on generally opposite edges of the distal end of the cutting tube 14. These first and second cutting edges 20, 22 are separated by a distance D, as shown in the distal end view of FIG. 3B. In the particular example shown in the drawings, the first and second cutting edges 20, 22 are located on opposite lateral sides of the distal end of the cutting tube 14 and a blunt, protruding tip 24 is located on the bottom of the distal end of the cutting tube. Also, a blunt edge 26 is located at the top of the distal end of the cutting tube 14. Thus, only the lateral cutting edges 20, 22 are sharp and intended to cut tissue. The blunt, protruding tip 24 can, in some applications, be configured and used to facilitate insertion of the device 10 to its intended location and/or the blunt protruding tip 24 may be placed in an anatomical or man made grove or channel (e.g., Schlemm's Canal of the eye) such that it will then advance through the channel or groove and guide the advancement and positioning of the remainder of the device 10.

Figure 6:
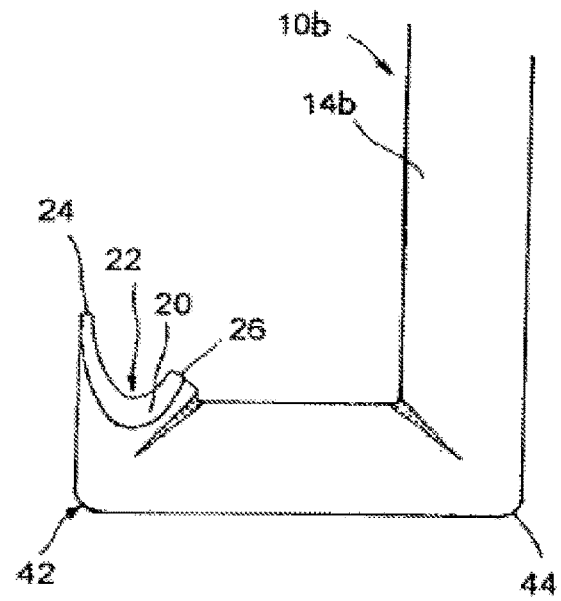
FIG. 6 is a side view of the distal portion of another embodiment of a needle cutter device of the present invention having a plurality of curves or bends formed in the cutting tube.

One or more bends or curves may optionally be formed in the cutting tube 14 to facilitate its use for its intended purpose. For example, in the embodiment of the device 10 shown in FIG. 2, a single bend 17 of approximately 90 is formed near the distal end of the cutting tube 14. In the embodiment of the device 10b shown in FIG. 6, two separate bends of approximately 90 degrees each are formed at spaced apart locations on the cutting tube 14, thereby giving the cutting tube 14 a generally U shaped configuration. It will be appreciated that any number of bends or curves, in any direction and of any severity may be formed in the cutting tube 14 to facilitate its use in specific procedures or to enable it to be inserted through tortuous anatomical channels of the body. In most cases, the degree of curvature in embodiments where a single bend or curve is formed will be between approximately 30 and approximately 90 degrees and in embodiments where more than one bend or curve are formed in the cutting tube 14 each such bend or curve will typically be between approximately 15 to approximately 90 degrees.

Figure 4:
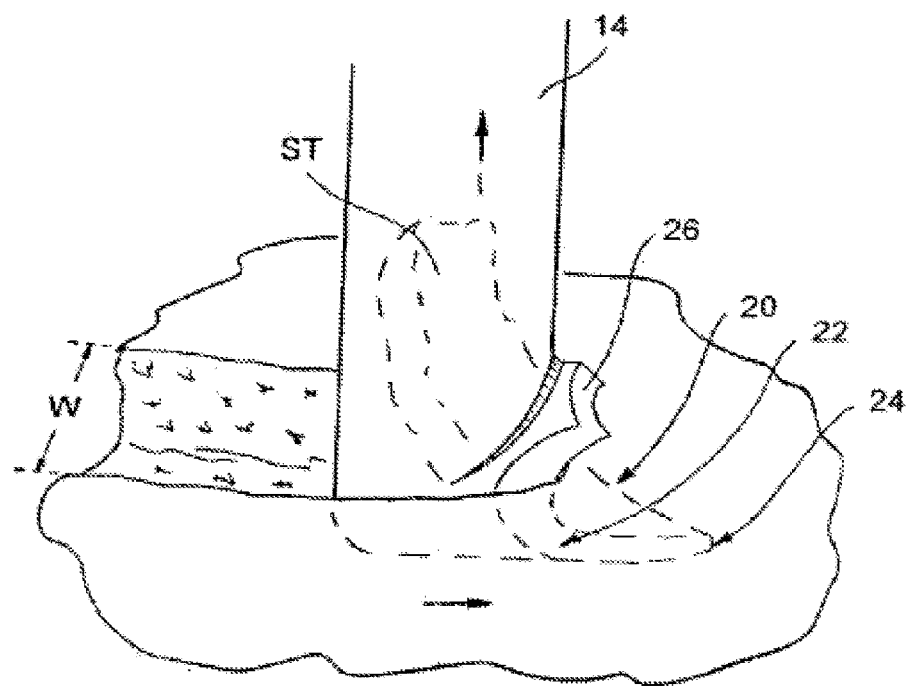
FIG. 4 is a side view of a distal portion of a needle cutter device of the present invention being used to cut a strip of tissue of approximate width W.

As shown in FIG. 4, when the cutting tube 14 is advanced through tissue, distal end first, the first and second cutting edges 20, 22 will cut a strip ST of tissue having approximate width W, such approximate width W being approximately equal to the distance D between the first and second cutting edges 20, 22. The severed strip ST of tissue will enter the lumen 27 of the cutting tube 14 as the device advances. Negative pressure may be applied to lumen 27 to aspirate the strip ST of tissue and/or fluid and/or other matter through lumen 27.

The device 10 may optionally include a second lumen. Such second lumen may be used for infusion of fluid through the device 10 or for other purposes. In the embodiment shown in FIGS. 1 and 2, the device 10 comprises an outer tube 16 in addition to the cutting tube 14. The cutting tube 14 is of smaller diameter than the outer tube 16 and the cutting tube 14 may extend through the lumen 19 of the outer tube 16 such that a distal portion of the cutting tube 14 extends out of and beyond the distal end of the outer tube 16, as may be seen in FIG. 2. The distal end of the outer tube 16 is tapered and in close approximation with the outer surface of the cutting tube 14. Fluid may be infused through the lumen 19 of the outer tube 16, through the space between the outer surface of the cutting tube 14 and the inner surface of the outer tube 16. Fluid that is infused through the lumen 19 of the outer tube 16 may flow out of one or more apertures 11 formed near the distal end of the outer tube.

Figure 5:
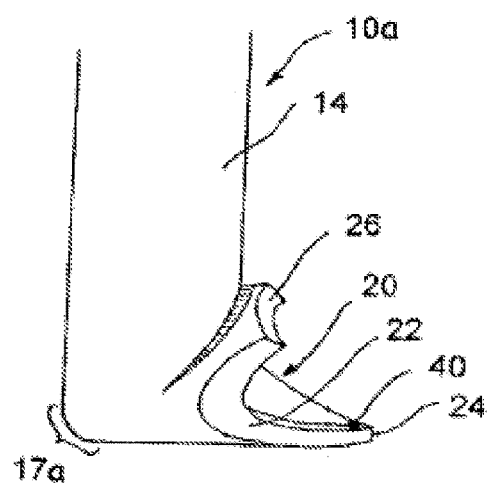
FIG. 5 is a perspective view of the distal portion of a needle cuter device of the present invention incorporating apparatus for severing a strip of tissue cut by the needle cutter device after the strip of tissue has reached a desired length.

In some embodiments, the device 10 may be equipped with severing apparatus for severing (e.g., transversely cutting or transecting) the strip ST of tissue to fully excise or detach the strip ST of tissue from the remaining tissue mass and/or from the body of a human or animal subject. Such severing apparatus may comprise any suitable type of tissue cutter such as a blade, scissor, guillotine, electrode(s), laser, energy emitting tissue cutter, mechanical tissue cutter, etc. FIG. 5 shows an example of an embodiment of the device 10a wherein monopolar or bipolar electrode(s) 40 are located on the distal end of the cutting tube 14. When it is desired to sever the strip ST of tissue, the electrode(s) is/are energized with sufficient energy to sever the strip ST, thereby disconnecting the strip ST from the remaining tissue mass and/or the body of the human or animal subject.

In some embodiments of the device 10, the cutting edges 20, 22 may be heated such that they will cauterize as the cut. As those of skill in the art will appreciate, such heating of the cutting edges 20, 22 may be accomplished by placement of electrode(s) near the cutting edges 20, 22 such that, when the electrode(s) is/are energized, the cutting edges 20, 22 will become heated to a temperature suitable for the desired cauterization function.

The needle cutter device 10 of the present invention may optionally be used as part of a system 12, as shown in FIG. 1. The basic components of the system 12 comprise an aspiration pump module 74 and a source of irrigation fluid 72, mounted on a surgical roller cart 70. Control of the console functions during procedures may be accomplished by an aspiration foot pedal 78 which controls an aspiration pump 74 and variation in the height of the source of infusion fluid 72 to change the gravity fed pressure or flow rate of infusion fluid through the device. A pinch valve, or other means, may also be incorporated in the console to control flow of the irrigation fluid to the needle cutter device 10. In embodiments that include apparatus (e.g., electrode(s)) for heating the cutting edges 20, 22 and/or for severing the strip ST of tissue (FIG. 5), the system 11 may additionally comprise an electrical current source, such as an electrosurgical generator 76 and electrosurgical foot pedal 80 which controls the electrosurgical generator to deliver desired amount(s) of energy to the electrode(s) or other electrical elements (e.g., resistance heater(s), etc.) on the device 10. As an option, all of the basic control functions of system 12 may be integrated into a single foot pedal to facilitate use.

The device 10 may be provided as a pre-sterilized, single-use disposable probe or tip that is attachable to a standard surgical irrigation/aspiration handpiece such as that commercially available as The Rhein I/A Tip System from Rhein Medical, Inc., Tampa, Fla. After the device 10 has been attached to the handpiece, it may be connected to any or all of the electrosurgical generator module 76, aspiration pump module 74 and the source of irrigation fluid 72, as shown. Thus, the device 10 may be fully equipped for irrigation, aspiration, and electrosurgical capabilities, as described herein.

Figure 3A:
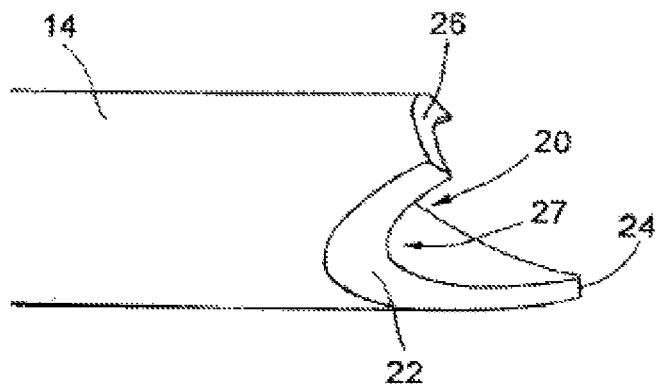
FIGS. 3A-3D show various steps in a method for manufacturing a needle cutter of the present invention.
Figure 3B:
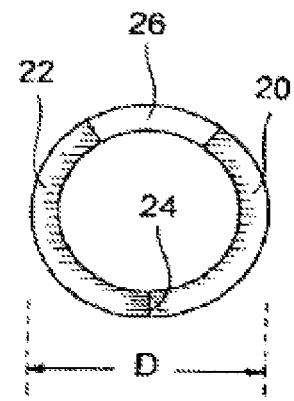
Figure 3C:
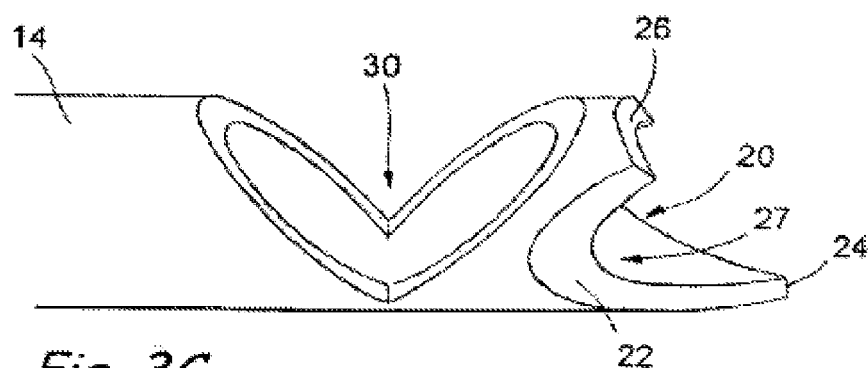
Figure 3D:
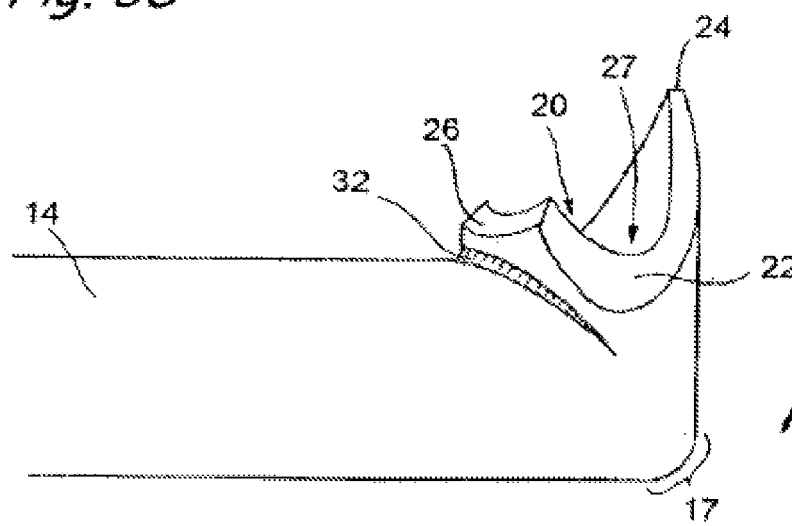

FIGS. 3A-3D show an example of a method for manufacturing the cutting tube 14 from standard tubing (e.g., stainless steel hypodermic tubing). Initially, the distal end of a tube is cut to form the lateral cutting edges 20, 22, the protruding tip 24 and the blunt top edge 26. Thereafter, if it is desired to have one or more bends or curves in the cutting tube 14, angular cut out(s) 30 may be formed in the tube 14, as shown in FIG. 3C. Thereafter, the tube 14 is bent to bring the edges of each angular cut out 30 into apposition and weld, adhesive or other joining techniques are used to weld or join the apposed edges of the cut outs together, thereby forming the desired bend(s) or curve(s) in the cutting tube 14. Likewise, if it is desired to have one or more bends or curves in the cutting tube 14, the tube 14 may be directly bent to form said curves or bends without the use of angular cut outs(s) 30. It may be appreciated that the use of angular cut-out(s) 30 allow a tube 10 of a given diameter to incorporate a curve or angle in a more compact form than is possible by bending tubing 10 of a given diameter to said curve or angle without kinking or damaging tube 10.

The device 10 and system 12 are useable to perform a variety of procedures wherein it is desired to form an incision or opening of a desired width or to remove, from a mass of tissue, a strip ST of tissue of a desired width.

One particular procedure that may be performed to treat glaucoma, using the device 10 and system 12 of the present invention, is a goniectomy. As explained herein a goniectomy procedure is an ab interno surgical procedure wherein a sector of the trabecular meshwork is removed from the eye of the patient to facilitate drainage of aqueous humor from the anterior chamber of the eye through Schlemm's Canal and the associated collector channels, thereby relieving elevated intraocular pressure.

To perform a goniectomy procedure using the device 10, first a small incision is made in the cornea at about 3 o'clock in the left eye, or at about 9 o'clock in the right eye. A 1.5 mm slit knife may be used to make this incision.

The device 10 is attached to the source of irrigation fluid 72 (e.g., basic balanced salt solution) such that irrigation fluid will flow through lumen 19 of the outer tube 16 and out of outflow aperture 11. The device 10 is then inserted through the incision and into the anterior chamber of the eye (with irrigation flowing). In some cases, during the insertion of the device 10, the source of irrigation fluid 72 may initially connected to the device such that the irrigation fluid will flow through the lumen 27 of the cutter tube 14. In this manner, irrigation fluid will begin to infuse into the anterior chamber of the eye as soon as the distal end of the cutter tube 14 has entered the anterior chamber, rather than being delayed until the larger outer tube 16 and aperture 11 have been advanced through the incision and into the anterior chamber. By this alternative approach, irrigation fluid may be caused to flow out of the distal end of the cutter tube 14 as the device 10 is being inserted, thereby spreading or opening the incision by hydraulic force while in addition increasing the fluid pressure in the anterior chamber. Such spreading or opening of the incision may facilitate advancement of the larger diameter outer tube 16 through the incision. Pressurizing the fluid in the anterior chamber causes the anterior chamber to deepen and may facilitate maneuvering of device 10 within the anterior chamber. In cases where this alternative approach is used, the source of infusion fluid 72 may be disconnected from lumen 27 of the cutter tube 14 after the device 10 has been inserted into the anterior chamber and, thereafter, the infusion fluid source 72 may be reconnected to lumen 19 of outer tube 16 such that infusion fluid will flow out of aperture 11. Negative pressure (e.g., via aspiration pump module 74) may then be applied to lumen 27 of the cutter tube 14 so as to aspirate fluid and debris through lumen 27 as shown in FIG. 4. The vertical height of the infusion fluid source 72 may be adjusted to provide sufficient gravity feed of infusion fluid to make up for the volume of fluid or matter being aspirated from the anterior chamber through lumen 27, thereby maintaining the desired pressure of fluid within the anterior chamber during the procedure.

A lens device (e.g., Ocular Swan-Jacob Autoclavable Gonioprism, Model OSJAG, Ocular Instruments Inc., Bellevue, Wash.) may be positioned on the anterior aspect of the eye to enable the physician to clearly visualize the angle of the eye where the segment of trabecular meshwork is to be removed. Under direct visualization, the device 10 is advanced until the distal tip of the cutter tube 14 is positioned adjacent to the trabecular meshwork at the location where the strip ST is to be removed. Thereafter, the protruding tip 24 is advanced through the trabecular meshwork and into Schlemm's Canal.

The device 10 is then advanced along Schlemm's Canal, thereby causing the cutting edges 20, 22 to cut a strip of the trabecular meshwork, thereby creating an opening through which aqueous humor may drain from the anterior chamber of the eye.

After a strip of tissue of the desired length (e.g., about 2-10 mm) has been cut by the lateral cutting edges 20, 22, any optional tissue severing apparatus (e.g., electrode(s) 40 may be used (if present) to transect or sever the strip ST of tissue thereby disconnecting it from the patient's body and allowing it to be aspirated or drawn into or through lumen 27.

Thereafter, the aspiration is stopped, the device 10 is removed from the eye, and the infusion is stopped.

Following completion of the surgery, aqueous humor will drain from the anterior chamber through the opening that was created by removal of the strip of tissue from the trabecular Meshwork™.

Although the invention has been described above with respect to certain embodiments and examples, it is to be appreciated that such embodiments and examples are non-limiting and are not purported to define all embodiments and examples of the invention. Indeed, those of skill in the art will recognize that various modifications may be made to the above-described embodiments and examples without departing from the intended spirit and scope of the invention and it is intended that all such modifications be included within the scope of the following claims.

The invention claimed is:

1. A dual blade device useable for performing an ab interno procedure within a human eye to remove a strip of trabecular meshwork tissue, said device comprising:
   a probe that extends along a first longitudinal axis;
   the probe further comprising a distal portion that extends along a second longitudinal axis, the distal portion connected to the first longitudinal axis by a bend in the probe of approximately 30 degrees to approximately 90 degrees relative to the first longitudinal axis of the probe,
   wherein the distal portion comprises a distal end comprising a transverse width, a top surface, a bottom surface, and a tip disposed on a bottom of the distal end, wherein said tip is tapered such that the transverse width of the distal end is narrowest at the tip and ends in a vertical edge;
   wherein the distal end further comprises first and second lateral cutting edges, wherein the first and second lateral cutting edges are separated by a gap having a distance D, and wherein the first and second lateral cutting edges are configured to simultaneously cut tissue that passes over the top surface of the distal portion and into contact with the first and second lateral cutting edges and wherein:

the bend between a portion of the probe that extends along the first longitudinal axis and the distal portion of the probe that extends along the second longitudinal distance comprises a rounded corner; and the distal portion is sized to fit within Schlemm's Canal of the human eye and, when so positioned, is advanceable through Schlemm's Canal such that trabecular meshwork tissue passes over its top surface and contacts the first and second lateral cutting edges.

2. The device according to claim 1, wherein the first and second lateral cutting edges are configured to cut a strip of trabecular meshwork tissue have a width W that is substantially equal to the distance D between said first and second lateral cutting edges.

3. The device according to claim 1 useable for cutting a sector of trabecular meshwork tissue having a length of 2 to 10 millimeters.

4. The device according to claim 1, wherein the bottom surface of the distal portion extends to form a curve of approximately 90 degrees relative to the first longitudinal axis of the probe.

5. A system comprising a device according to claim 1 in combination with a 1.5 mm slit knife for forming said incision in the human eye.

6. The device according to claim 1 wherein the device is manually operable to remove a strip of trabecular meshwork tissue.

7. The device according to claim 1, wherein the bottom surface of the distal portion is round.

* * * * *